United States Patent [19]

Makita et al.

[11] Patent Number: 5,037,614
[45] Date of Patent: Aug. 6, 1991

[54] CHEMICAL LEVEL MEASUREMENT DEVICE WITH EASY ACTION COVER AND SINGLE CONTROL MODE SELECTION CAPABILITY

[75] Inventors: Shigeru Makita; Tamio Miyake; Yoshihiko Sano, all of Kyoto, Japan

[73] Assignee: Omron Tateisi Electronics Co., Kyoto, Japan

[21] Appl. No.: 504,025

[22] Filed: Mar. 27, 1990

Related U.S. Application Data

[63] Continuation of Ser. No. 72,817, Jul. 13, 1987, abandoned.

[30] Foreign Application Priority Data

Jul. 15, 1986 [JP] Japan .............................. 61-167186
Jul. 15, 1986 [JP] Japan .............................. 61-167187

[51] Int. Cl.[5] ..................... G01N 21/00; G01N 33/50; G01N 35/00; G01J 3/46
[52] U.S. Cl. ................................... 422/68.1; 422/62; 422/82.05; 436/46; 436/48; 356/402
[58] Field of Search ............... 422/68, 62, 68.1, 82.05; 436/46, 48; 356/402

[56] References Cited

U.S. PATENT DOCUMENTS 4,589,774  5/1986  Dupree et al. .................... 356/440

FOREIGN PATENT DOCUMENTS 0183524  6/1986  European Pat. Off. .
2096314  10/1982  United Kingdom .

*Primary Examiner*—David L. Lacey
*Assistant Examiner*—Kimberly A. Trautman
*Attorney, Agent, or Firm*—Fish & Richardson

[57] ABSTRACT

This device measures the level of a certain chemical in a liquid infiltrated into a piece of test paper impregnated with a test chemical the optical properties of which alter according to the level of the certain chemical. It includes: a test paper holder, provided in a test paper insertion unit provided in a casing; a device for emitting light and a device for sensing light, both provided to oppose a piece of test paper held by the holder; a cover, slidably mounted to the casing, for selectably covering over the insertion unit; a device for biasing this cover in one direction; a device for engaging this cover in an extreme position in the opposite direction; and a device for releasing the engagement of the engaging device. This engagement releasing device may be a press button provided to the casing; and the sliding direction of the cover may be its opening direction of movement, or alternatively may be its closing direction of movement. Alternatively, this device may include a device for emitting light and a device for sensing light, both provided to oppose a piece of test paper, and a switch for selecting between an action mode for executing a measurement action and at least one other mode for performing some other function, these modes being switched between every time this mode selection switch is actuated. Optionally, at least three such modes may be switched between in a cyclical sequence. The mode selection switch may include a mode selection button.

11 Claims, 10 Drawing Sheets

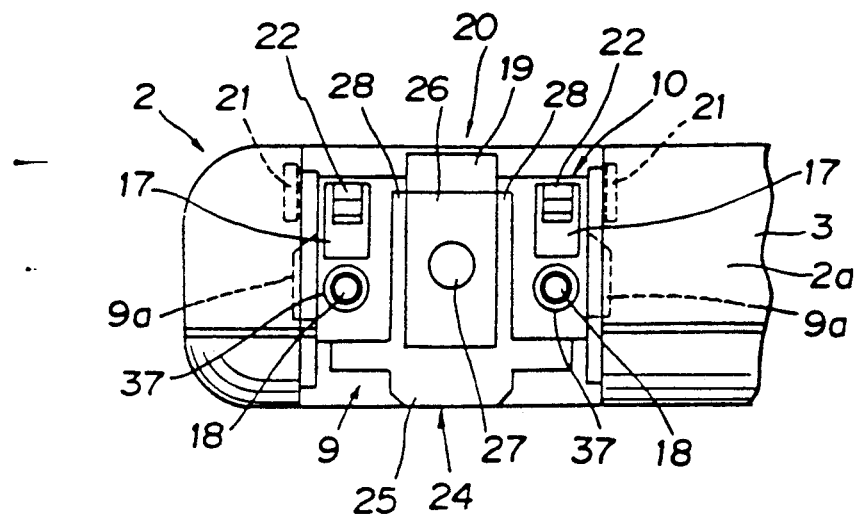
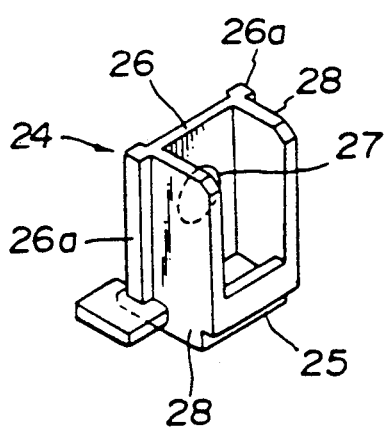
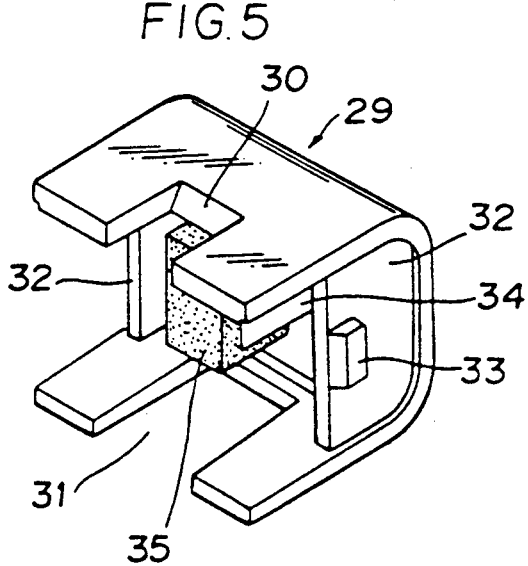

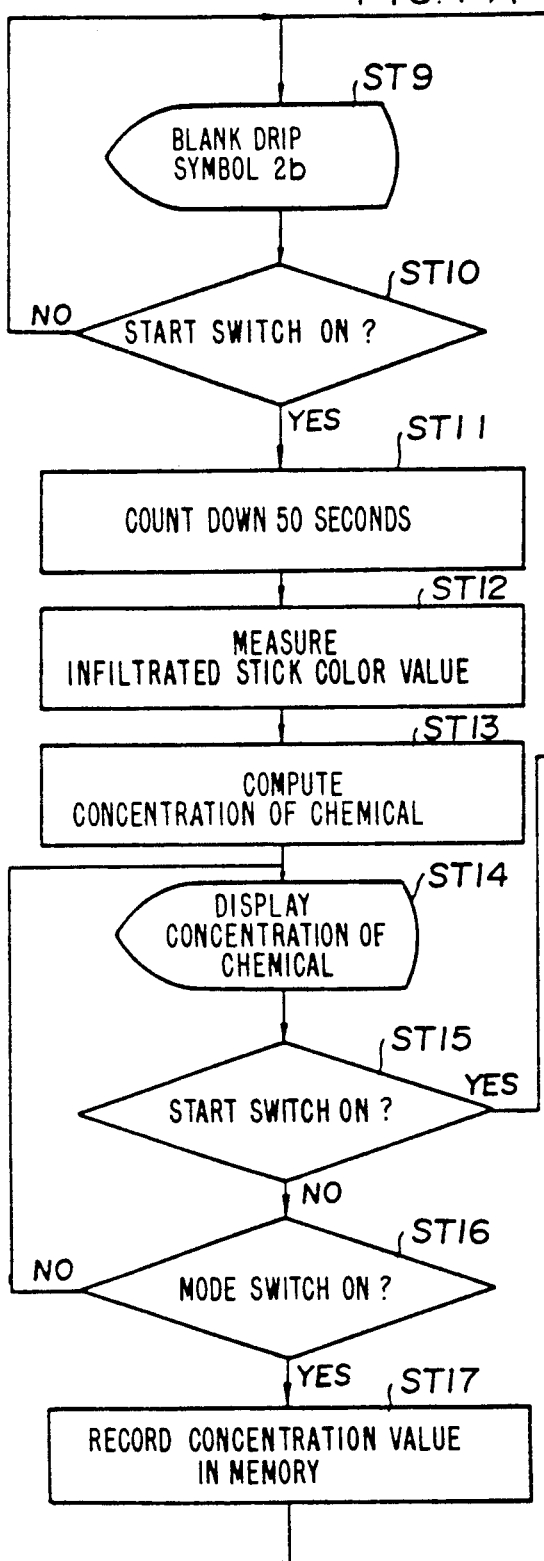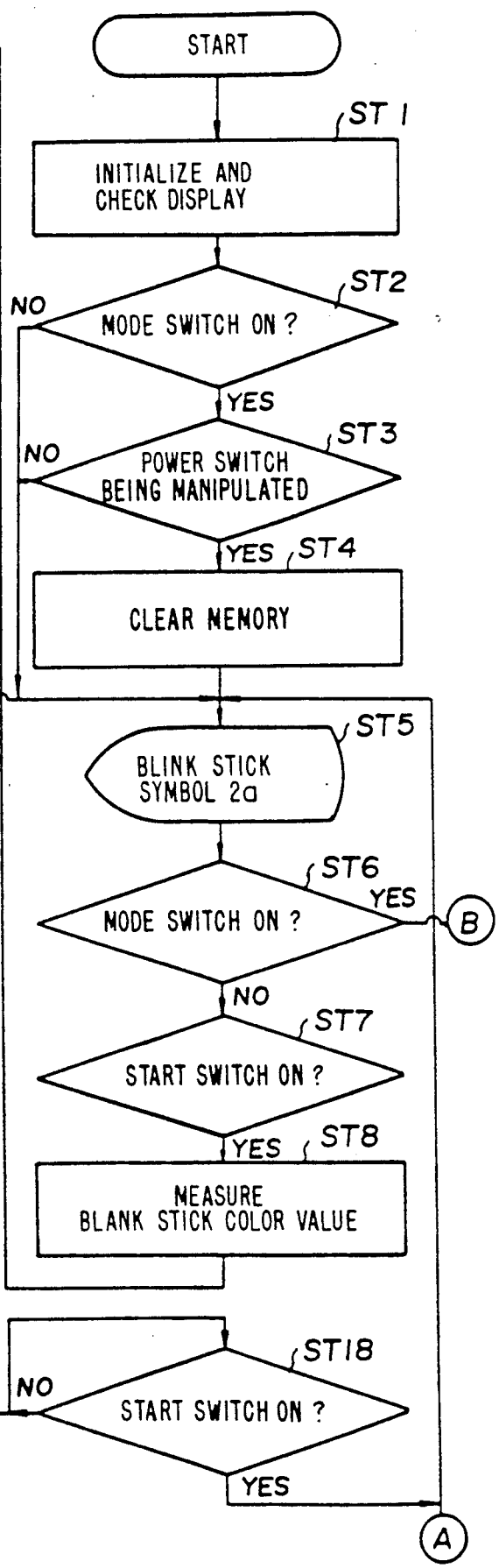
FIG. 7A

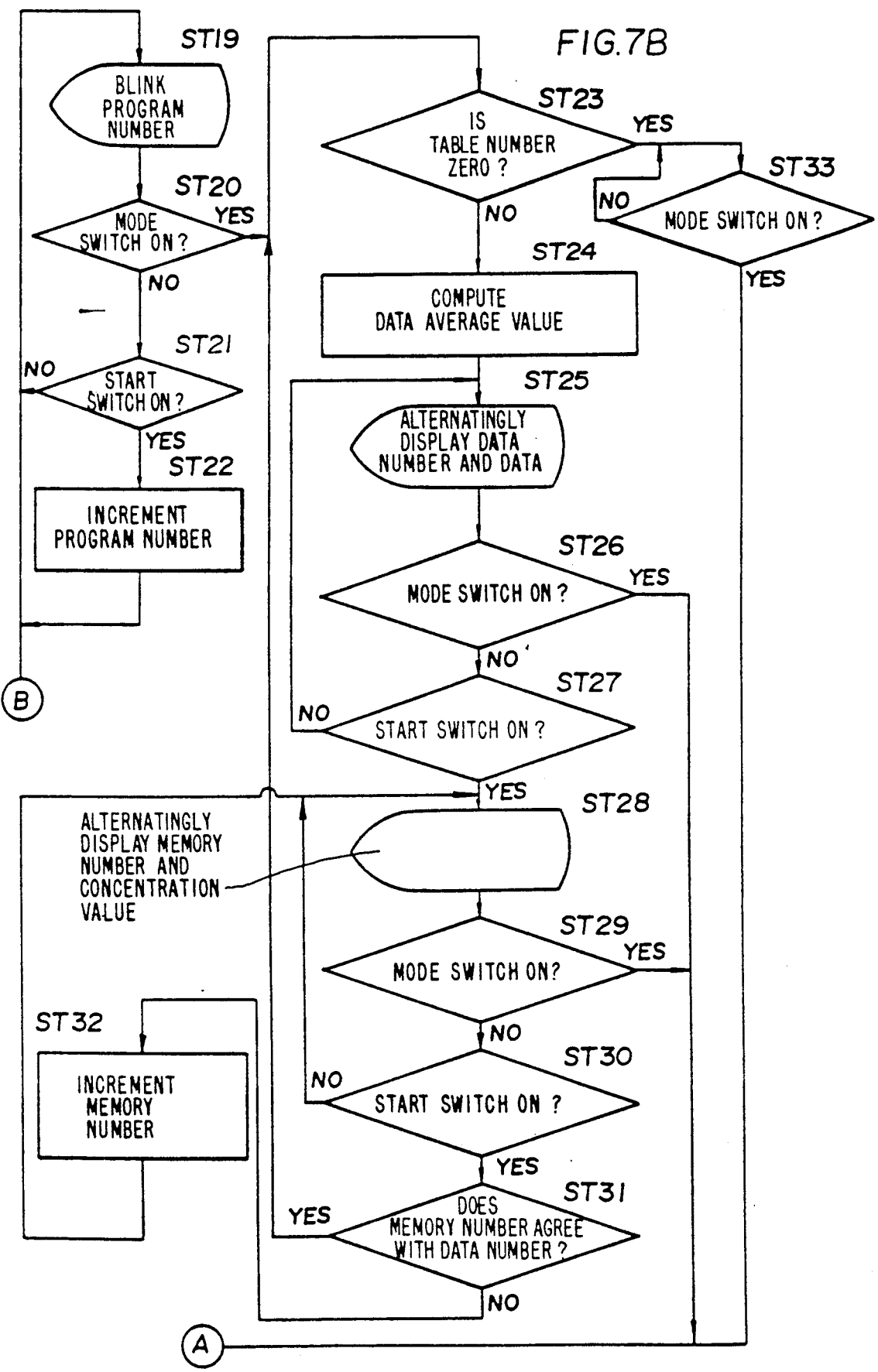

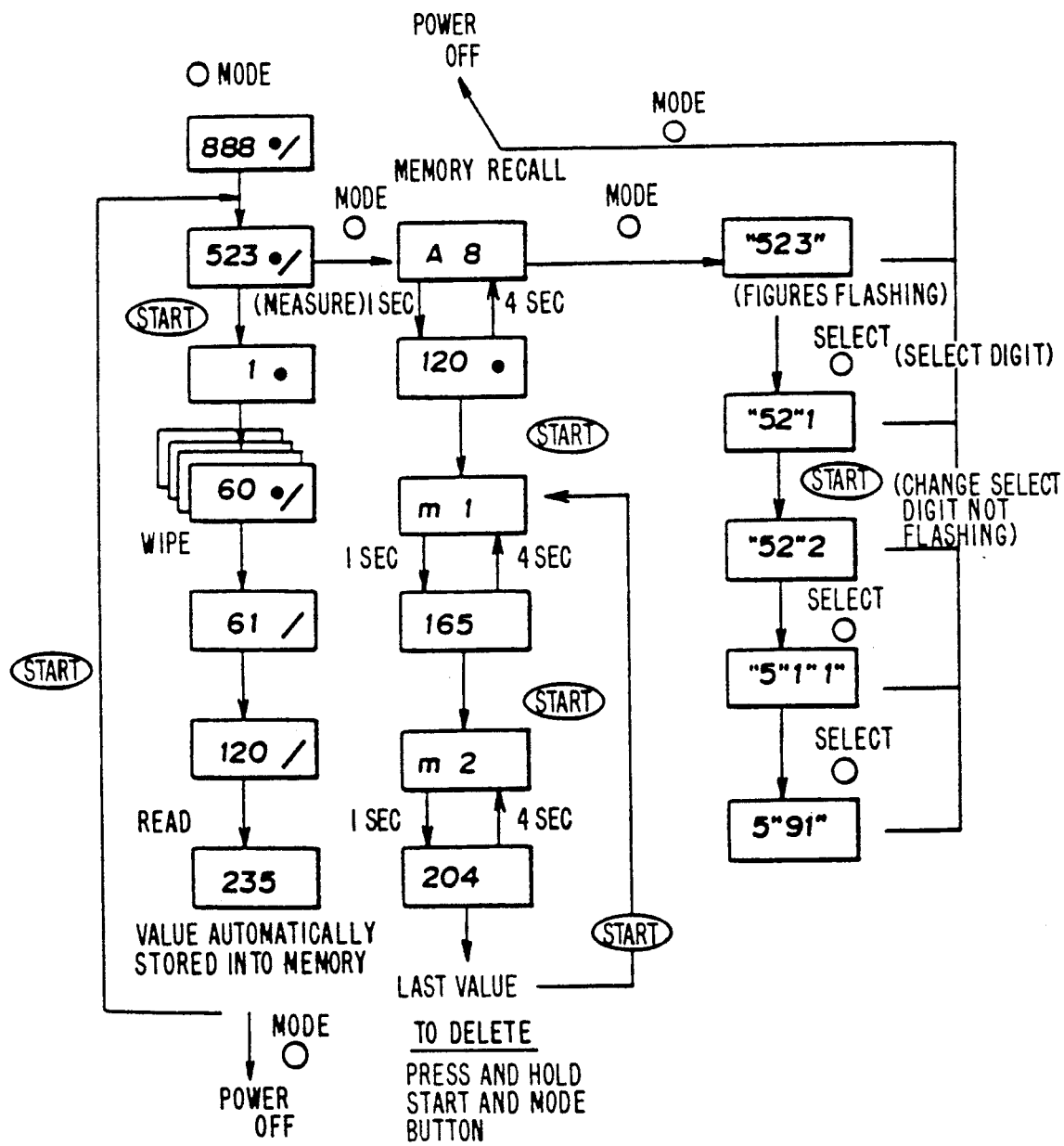

5,037,614

CHEMICAL LEVEL MEASUREMENT DEVICE WITH EASY ACTION COVER AND SINGLE CONTROL MODE SELECTION CAPABILITY

This application is a continuation of U.S. application Ser. No. 07/072,817, filed July 13, 1987, now abandoned.

BACKGROUND OF THE INVENTION

The present invention relates to a device for the measurement of the level of a chemical in a body fluid of a subject, and particularly relates to such a chemical level measurement device which is suitable for easily and conveniently measuring the level of blood sugar or urine sugar or the like.

A per se conventional such device for the measurement of the level of a chemical, such as typically sugar level, in a body fluid, such as blood or urine, of a subject is operated as follows. A piece of test paper, impregnated beforehand with a test chemical, is infiltrated with a sample of the body fluid, such as blood or urine or the like, of the subject; this test chemical should be one which reacts in a visible manner, as by changing its color or some other of its optical properties, according to the level or concentration of the relevant chemical, the level of which is to be measured, in the body fluid of the subject. Then this piece of test paper is fitted to a biochemical level measurement device, and the color or other optical property thereof is measured by said device, so as to assess the actual value of the concentration of said relevant chemical in the body fluid of the subject, i.e. so as to quantitatively evaluate the concentration of said relevant chemical. And various biochemical level measurement devices which evaluate one or more of the optical properties of such a treated piece of test paper, and which perform appropriate computations for deriving the concentration of the relevant chemical substance in the body fluid of the subject, are currently available.

Particularly, such a per se conventional biochemical level measurement device typically comprises a measurement circuit of an electronic type, and a display unit, both of these being mounted to its case, and further is provided with a test paper insertion unit which is constituted by a depression or aperture formed in its said case. This test paper insertion unit is typically provided with a test paper holding unit for holding the test paper —which typically for ease of handling is mounted on the end of a strip of flexible plate, the whole being termed a "test stick"—and with a light emitting element for illuminating said test paper and with a light receiving unit for receiving light which has been affected by said test paper, either by the action of reflection or by the action of transmission. And, typically, a cover of the test paper insertion unit can be selectively opened and closed, in order to prohibit the ingress of light from the outside of the device, which otherwise would disturb the result of the measurement.

Such a per se conventional biochemical level measurement device is capable of assessing the illumination reflected from the test paper which is impregnated with the test chemical and is infiltrated with the sample of the body fluid of the subject, or alternatively is capable of assessing the illumination transmitted through said test paper, and therefrom said device quantitatively assesses the concentration in said body fluid sample of the particular chemical substance which is being analyzed for. The result of this concentration evaluation is displayed on the display unit as a digital or as an analog value.

PROBLEMS WITH THE PHYSICAL CONSTRUCTION OF THE PRIOR ART

However, this prior art type of biochemical level measurement device is subject to the following problems with regard to its physical construction and operation.

Typically, in such a prior art type of biochemical level measurement device, the cover of the test paper insertion unit is selectively opened and closed by being hinged upon a hinge shaft and by being pivoted around such a hinge shaft by the hand of the operator of the device. In other words, the opening and closing of such a hinged cover of the test paper insertion unit is typically performed manually. Therefore, when a piece of test paper is to be inserted into the test paper insertion unit, which is typically positioned as resting upon the upper surface of a table or a desk or the like, the operator first must open the cover of the test paper insertion unit by turning it about its hinge in one direction, and then must hold the test paper piece in position while closing said cover of the test paper insertion unit by turning it about its hinge in the reverse direction to said one direction. Such an operation typically requires the use of two hands by the operator, one for holding the test paper piece in position and the other for closing said cover of said test paper insertion unit.

However nowadays, along with the ever progressing tendency towards miniaturization of all types of electronic devices, such biochemical level measurement devices are constantly being made smaller and lighter. Since such a biochemical level measurement device is typically positioned as resting upon the upper surface of a table or a desk or the like, and is not typically secured to such a positioning surface, the problem has arisen that, particularly during the processes of opening and of closing the cover of the test paper insertion unit, the biochemical level measurement device tends to slip around on such a positioning surface. Such movement of the device can lead to improper fitting of the test paper into the test paper insertion unit, which can deteriorate the accuracy of the measurement process and in an extreme case can can render said measurement process impossible. Accordingly, it is often found to be desirable to hold the biochemical level measurement device in place on the positioning surface on which it is lying for use. This however is difficult, because as described above particularly the process of closing the cover of the test paper insertion unit while simultaneously holding the test paper piece in position itself typically requires the use of two hands by the operator, and, if additionally the biochemical level measurement device is required to be h held in place on the positioning surface on which it is lying for use, then in principle a third hand is required for this action. Since no individual operator has three hands, either the assistance of a second operator is required, which is very inconvenient, or alternatively two of the above described three operations must be performed with the same hand of the operator, which can be a very clumsy and troublesome procedure. This problem is aggravated in the case that the operator and the subject are one and the same person and that the body fluid which is being tested is blood which has been drained from a finger of the operator/subject by pricking said finger, because in such a case this finger, being wounded, is not really suitable for performing fiddly manipulations of the cover of the test paper insertion unit or the like.

A subsidiary physical problem with the type of prior art construction outlined above is that a weak point of the device is set up at the point where the cover of the test paper insertion unit is hinged to the casing thereof, and stress at such a point, inevitably generated when the cover is opened or closed, may in time damage or crack said casing.

PROBLEMS WITH THE ELECTRONIC CONSTRUCTION OF THE PRIOR ART

To expound in more detail the operation of this prior art type of biochemical level measurement device, generally first a piece of test paper, impregnated beforehand with a test chemical, but fresh and not yet infiltrated with any sample of the body fluid, is fitted to this biochemical level measurement device, and the color or other optical property thereof is measured by said device, so as to assess a base optical property value for such test paper when infiltrated with a zero amount of the body fluid. Subsequently, this piece of test paper is infiltrated with a sample of the body fluid, such as blood or urine or the like, of the subject, and thereby the test chemical impregnated into this test paper piece reacts in a visible manner, i.e. by changing its color or other optical property, according to the level or concentration of the relevant chemical, the level of which is to be measured, in this sample of the body fluid of the subject. This infiltrated piece of test paper is then in its turn fitted to this biochemical level measurement device, and the color or other optical property thereof is again measured by said device, so as to assess an optical property value for such test paper when infiltrated with the body fluid sample. By comparing the two optical property values thus obtained, for example by calculating their ratio, the actual value of the concentration of said relevant chemical in the body fluid sample of the subject may be determined, according to a reference table which may be stored in the biochemical level measurement device in advance. And, typically, the thus determined value for the concentration of said relevant chemical in the body fluid sample of the subject is displayed upon a display device.

However, this prior art type of biochemical level measurement device is subject to the following problems with regard to its electronic construction and operation. Namely, the actual optical properties of the test paper are known to vary from one production lot thereof to another. Accordingly, the optical properties of two different pieces of test paper which are taken from two different production lots may be different, even if they are infiltrated with portions of the same body fluid sample of the same subject which contain identical concentrations of said relevant chemical. Therefore, if the same reference table is utilized for the above calculation to derive the actual value of the concentration of said relevant chemical, different results will be obtained. Accordingly, it is desirable to utilize different reference tables for test paper pieces which are taken from different production lots of test paper. Thus, it would be convenient to store various different ones of these different reference tables in memory of the biochemical level measurement device, and to select one or another of these different reference tables according to the particular piece of test paper which is to be used, i.e. according to a particular action mode (or program mode) for the biochemical level measurement device.

Further, it would be convenient if the results of measurement were stored as they were obtained, so that they may be retrieved, according to a particular action mode (or memory mode) for the biochemical level measurement device.

However, conventionally, there has never been provided any such biochemical level measurement device which is provided with various modes such as a program mode and a memory mode, in addition to its normal measurement action mode, and accordingly the diversified needs of the users of such a biochemical level measurement device have not in the past been fully met.

Further, even if such a concept of allowing of a plurality of action modes for such a biochemical level measurement device were implemented, if this were done by providing a plurality of different keys for the control of each individual one of such action modes, since there is inevitably a restriction on the available space for installing individual keys on the control panel or console of such a device, the inconvenience of operation thereof and the manufacturing cost thereof would be undesirably raised.

SUMMARY OF THE INVENTION

Accordingly, there has become evident a requirement for an improved chemical level measurement device with an improved physical construction. This problem has exercised the ingenuity of the inventors of the present invention.

Thus, it is one primary object of the present invention to provide a chemical level measurement device, which avoids the various problems detailed above with regard to its physical construction.

It is a further object of the present invention to provide such a chemical level measurement device, which can be easily operated.

It is a further object of the present invention to provide such a chemical level measurement device, which allows of easy and accurate placing of a test paper into a test paper insertion unit thereof.

It is a further object of the present invention to provide such a chemical level measurement device, the manipulation of which does not render it desirable for the operator to have three hands.

It is a further object of the present invention to provide such a chemical level measurement device, which while being light in weight and small in size is not subject to moving around during use upon the surface on which it is placed.

It is a further object of the present invention to provide such a chemical level measurement device, the use of which does not require the assistance of a second operator.

It is a further object of the present invention to provide such a chemical level measurement device, which is suitable to be used by an operator whose finger is currently in a wounded state by having been pricked for obtaining of a sample of blood for chemical level measurement by said device.

It is a further object of the present invention to provide such a chemical level measurement device, which is strongly built.

It is a further object of the present invention to provide such a chemical level measurement device, which is not subject to damage over a period of time.

According to a first aspect of the present invention, these and other objects are attained by a device for measuring the level of a certain chemical in a liquid which has infiltrated a piece of test paper impregnated with a test chemical the optical properties of which alter according to the level of said certain chemical, comprising: (a) a casing; (b) a test paper insertion unit, provided in the casing; (c) a test paper holder, provided in said test paper insertion unit; (d) a means for emitting light, provided to oppose a piece of test paper when held by said test paper holder; (e) a means for sensing light, provided to oppose a piece of test paper when held by said test paper holder; (f) a test paper insertion unit cover, slidably mounted to said casing, which according to sliding movement thereof either, when said test paper insertion unit cover is in a so called closed position, covers over said test paper insertion unit, or, when said test paper insertion unit cover is in a so called opened position, exposes said test paper insertion unit; (g) a means for biasing said test paper insertion unit cover in one sliding direction thereof; (h) a means for engaging said test paper insertion unit cover in an extreme position in the direction opposite to said sliding direction thereof; and: (i) a means for releasing the engagement of said engaging means for said test paper insertion unit cover.

According to such a chemical level measurement device as specified above, the action of opening or of closing the test paper insertion unit cover, as the case may be, can be accomplished simply by manipulating the engagement of the engagement releasing means. When this is done, the test paper insertion unit cover is automatically opened or closed, as the case may be, by the biasing force supplied by the biasing means. Further, since the reverse action, i.e. either closing or opening as the case may be, can simply be accomplished by pushing the test paper insertion unit cover with one finger, which conveniently may be a finger of the same hand of the operator that is simultaneously holding the casing of the device down to stop it sliding around on a surface on which it rests, thereby the operation of the device is made easy, because the other hand of the operator is left free for holding the test paper piece in place, and accordingly it is not required for the operator to have three hands. Thus, this chemical level measurement device can be easily operated, and allows of easy and accurate placing of a test paper into the test paper insertion unit thereof. Further, this chemical level measurement device, while being light in weight and small in size, is not subject to moving around during use upon the surface on which it is placed, and yet during use does not require the assistance of a second operator for holding it down or the like. Accordingly, this chemical level measurement device is suitable to be used by an operator whose finger is currently in a wounded state by having been pricked for obtaining of a sample of blood for chemical level measurement by said device. Further, because, even when an undue stress is applied to the chemical level measurement device, concentration of stress upon the casing thereof is reduced by being applied via a sliding engagement of the cover to the casing, as opposed to the pivoting type of engagement which was utilized in the prior art and which constituted a weak point, accordingly this chemical level measurement device is strongly built and is not subject to damage over a period of time.

And, according to a particular specialization of the present invention, the above and other objects may more particularly be accomplished by such a chemical level measurement device as specified above, wherein said means for releasing the engagement of said engaging means for said test paper insertion unit cover is a press button provided to said casing. Further, as a further or alternative specialization of the present invention, said sliding direction of said test paper insertion unit cover may be the direction of movement thereof towards said opened position thereof, or alternatively may be the direction of movement thereof towards said closed position thereof. Yet further, said test paper holder may be slidably mounted to said test paper insertion unit and may be selectively detachable therefrom.

Further, as detailed above, there has become evident a requirement for an improved chemical level measurement device with an improved electronic construction. This problem has also exercised the ingenuity of the inventors of the present invention.

Thus, it is another primary object of the present invention to provide a chemical level measurement device, which avoids the various problems detailed above with regard to its logical and electronic construction.

It is a yet further object of the present invention to provide such a chemical level measurement device, which allows selection of modes thereof other than a measurement action mode thereof.

It is yet further object of the present invention to provide such a chemical level measurement device, which allows selection of a program mode thereof.

It is a yet further object of the present invention to provide such a chemical level measurement device, which allows selection of a memory mode thereof.

It is a yet further object of the present invention to provide such a chemical level measurement device, which allows selection between said modes thereof in a simple fashion.

It is a yet further object of the present invention to provide such a chemical level measurement device, which allows selection between said modes thereof without requiring the provision of a large plurality of keys.

It is a yet further object of the present invention to provide such a chemical level measurement device, which allows selection between said modes thereof without requiring a large space for the mounting of control keys.

It is a yet further object of the present invention to provide such a chemical level measurement device, which is low in manufacturing cost.

It is a yet further object of the present invention to provide such a chemical level measurement device, which is convenient to use.

It is a yet further object of the present invention to provide such a chemical level measurement device, which meets the diversified requirements of users.

According to another second aspect of the present invention, these and other objects are attained by a device for measuring the level of a certain chemical in a liquid which has infiltrated a piece of test paper impregnated with a test chemical the optical properties of which alter according to the level of said certain chemical, comprising: (a) a means for emitting light, provided to oppose a piece of test paper; (b) a means for sensing light, provided to oppose said piece of test paper; and: (c) a means for selecting between an action mode for executing said measurement action and at least one other mode for performing some other function, said modes being switched between every time said mode selection means is actuated.

According to such a chemical level measurement device as specified above, since the various action modes may be selected between by the use of only one means, the mode selection means, thereby selection between said modes thereof may be made in a simple fashion, without requiring the provision of a large plurality of keys, and without requiring a large space for the mounting of control keys. Accordingly, this chemical level measurement device is low in manufacturing cost, also is convenient to use, and further meets the diversified requirements of users.

And, according to a particular specialization of the present invention, the above and other objects may more particularly be accomplished by such a chemical level measurement device as specified above, wherein at least three such modes are provided, and said three modes are switched between in a cyclical sequence, every time said mode selection means is actuated And, alternatively or conjointly, said mode selection means may comprise a mode selection button.

BRIEF DESCRIPTION OF THE DRAWINGS

The present invention will now be described with respect to the preferred embodiments thereof, and with reference to the illustrative drawings appended hereto, which however are provided for the purposes of explanation and exemplification only, and are not intended to be limitative of the scope of the present invention in any way, since this scope is to be delimited solely by the accompanying claims. With relation to the figures, spatial terms are to be understood as referring only to the orientation on the drawing paper of the illustrations of the relevant elements, unless otherwise specified; like reference symbols, unless otherwise so specified, denote the same parts and gaps and spaces and flow chart steps and so on in the various figures relating to one preferred embodiment, and like parts and gaps and spaces and flow chart steps and so on in figures relating to different preferred embodiments; and:

FIG. 3 is a front view of a test stick insertion unit included in said first preferred embodiment of the chemical level measurement device of the present invention, with said insertion unit cover thereof being removed;

FIG. 4 is a perspective view of a test stick holder assembly included in said first preferred embodiment;

FIG. 5 is a perspective view of the aforementioned insertion unit cover included in said first preferred embodiment;

FIGS. 7A–7B is a flow chart for explaining the operation of a micro processor incorporated in a controller which is included in the electronic constitution of the first preferred embodiment of the chemical level measurement device of the present invention;

FIG. 10 is a flow chart, similar to FIG. 7 but more cursory, for explaining the operation of a micro processor incorporated in a controller which is included in the electronic constitution of the second preferred embodiment of the chemical level measurement device of the present invention.

DESCRIPTION OF THE PREFERRED EMBODIMENTS

The present invention will now be described with reference to the preferred embodiments thereof, and with reference to the figures.

OVERALL PHYSICAL STRUCTURE OF THE FIRST PREFERRED EMBODIMENT

Figure 6A:
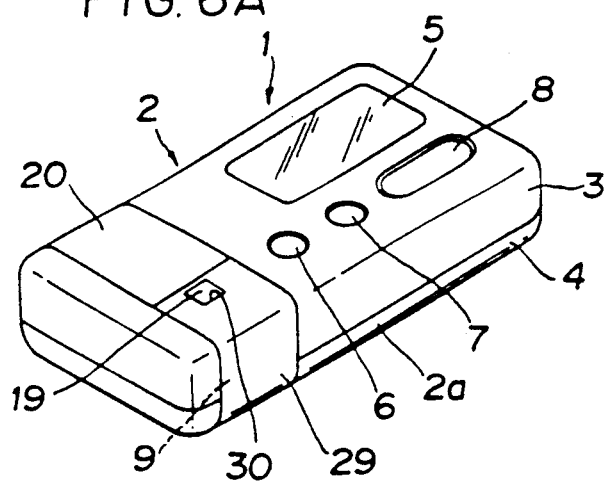
FIG. 6a is a perspective view of this first preferred embodiment of the chemical level measurement device of the present invention as a whole, shown in its state with said insertion unit cover thereof being in the closed condition and with no test stick being inserted into its test stick insertion unit.

FIG. 6a shows the overall physical structure of the first preferred embodiment of the chemical level measurement device of the present invention, in schematic perspective view, in the quiescent state of said device; this first preferred embodiment is, in fact, a device for measuring the level of sugar in a sample of the blood of a subject. In this figure, the reference numeral 1 denotes this first preferred embodiment of the chemical level measurement device of the present invention as a whole, while 2 denotes a case assembly thereof. This case assembly 2 consists of a combination of an upper case member 3 and a lower case member 4, which are sandwiched together with various internal components of the chemical level measurement device 1, not shown in FIG. 6 but to be partially detailed hereinafter, being housed between them.

On the upper surface as seen in FIG. 6a of the upper case member 3 there are provided an LCD display unit 5, a power switch 6, a mode switch 7, and a start switch 8. The mode switch 7 is for storing the value of blood sugar as determined and as displayed on the LCD display unit 5 in a memory device not shown in the figure.

Figure 1A:
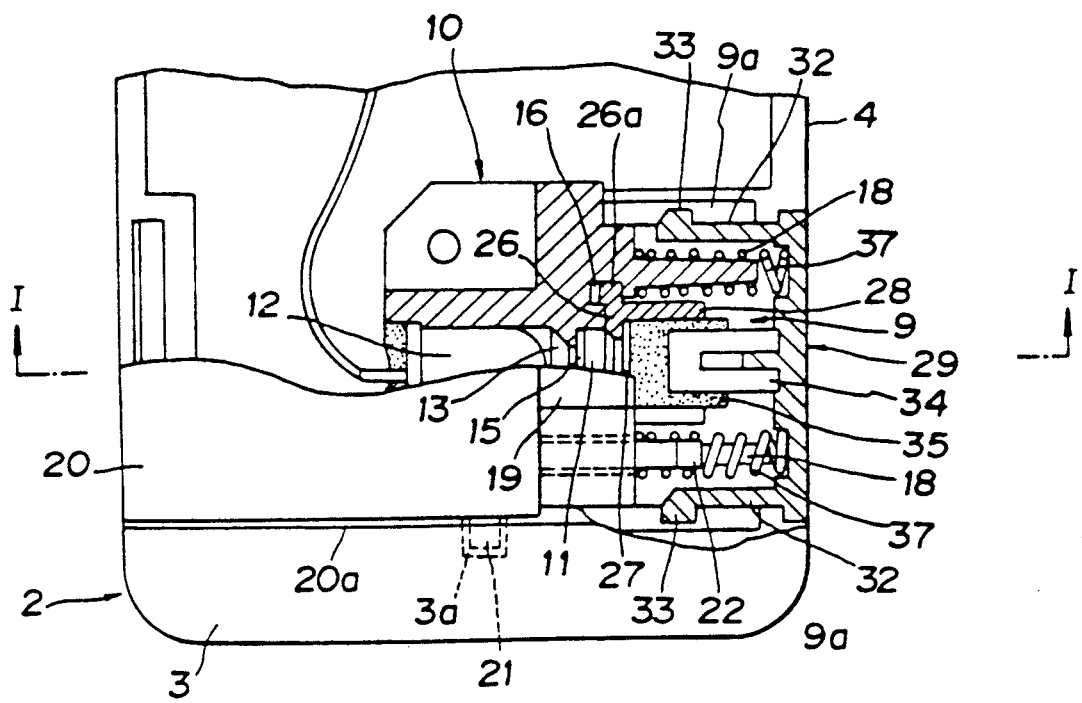
FIG. 1a is an enlarged partly broken away part sectional view, taken in a horizontal sectional plane with regard to the preferred orientation during use, of the first preferred embodiment of the chemical level measurement device of the present invention, as shown with an insertion unit cover thereof in the closed condition.
Figure 1B:
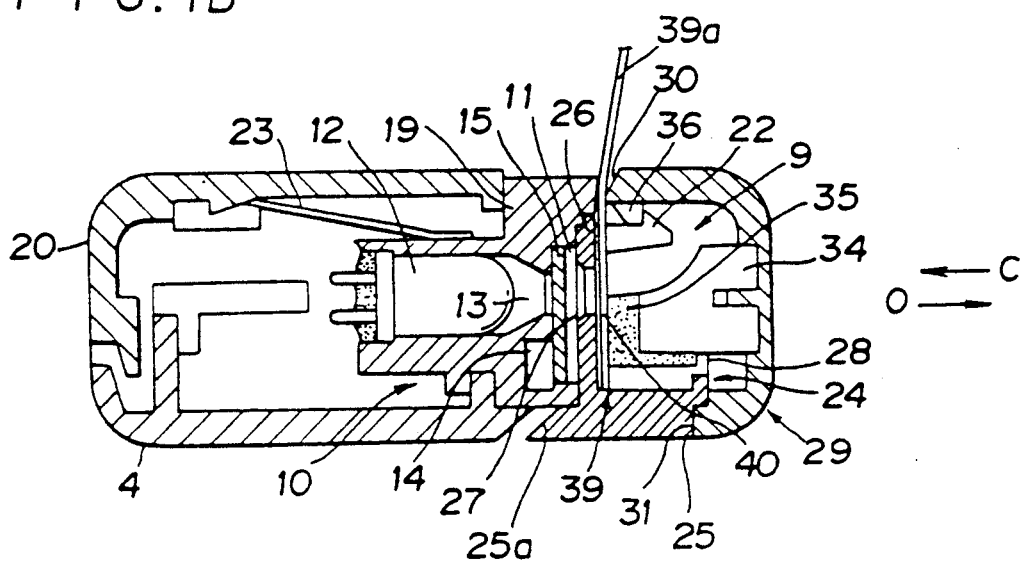
FIG. 1b is an enlarged sectional view, taken in a vertical sectional plane with regard to said preferred orientation during use and shown by the arrows I—I in FIG. 1a, of said first preferred embodiment of the chemical level measurement device of the present invention, as shown with said insertion unit cover thereof in the closed condition, and with a test stick inserted thereinto.

Referring now to FIGS. 1a and 1b, towards one of the ends of the case assembly 2, on its edge portion 2a, there is provided a test stick insertion unit 9, which is covered over by an insertion unit cover 29. When said cover 29 of said test stick insertion unit 9 is removed as will be described hereinafter, a sensor housing 10 is exposed. Hereinafter the direction of the apparatus to the right as seen in FIGS. 1a, 1b, 2a, and 2b will be spoken of as the front, so as to correspond with the general orientation of said apparatus during use thereof.

On the front surface of the sensor housing 10 there is formed a depression 11. Further, to said sensor housing 10 there are fitted a light emitting diode 12 (referred to as a "means for emitting light" in the claims of this specification) and a phototransistor 14 (referred to as a "means for sensing light" in the claims). The light emitting diode 12 is located in a communication aperture 13 which opens to one portion of said depression 11, while the phototransistor 14 is directly located at a position in said depression 11 offset somewhat from said communication aperture 13. And the bottom of the depression 11 is covered over with a transparent plate 15, which accordingly covers over the communication aperture 13 and the phototransistor 14 and protects them, thus preventing any of the test liquid such as blood or urine or the like from being able to wet or to adhere to said communication aperture 13 and said phototransistor 14.

Behind the test stick insertion unit 9 on the upper surface of the upper case member 3 there is provided an opening button member 20 (referred to as a "means for releasing engagement" in the claims). On the two opposite sides of said opening button member 20 there are formed guide pieces 21, best seen in FIG. 1a and in FIG. 3, which are slidably fitted into corresponding guide grooves 3a formed in the upper case member 3, so that the opening button member 20 can be moved in the vertical direction (with reference to the orientation of the apparatus shown in FIG. 1b, for example) with respect to said upper case member 3 and with respect to the lower case member 4 through a certain fairly small distance. And the opening button member 20 is biased in the upwards direction in the sense of the figures with respect to said upper and lower case members 3 and 4 by a sheet spring 23, which is fitted between a portion of said opening button member 20 and the upper surface of the rear portion of the sensor housing 10. In its thus upwardly biased position, the upper (i.e., the outer) surface of the opening button member 20 is positioned substantially flush with the upper and outer surface of the upper case member 3, as shown in, for example, FIGS. 3 and 6a.

Projecting in the forward direction (rightwards in FIGS. 1a and 1b) from the opening button member 20 there are provided two engagement rods 22 (referred to as "means for engaging" in the claims) with engagement pawls formed at their extreme ends. These engagement rods 22 are passed through vertically extending slots 17 formed in the sensor housing 10 and reach the interior of the test stick insertion unit 9, as shown in FIGS. 1a, 1b, and 3.

The reference numeral 24 denotes a test stick holder assembly, shown in perspective view in FIG. 4 and in sectional views in FIGS. 1a and 1b. This test stick holder assembly 24 comprises a holder assembly base 25, a test stick support plate 26 which rises substantially perpendicularly from said holder assembly base 25, and two holder assembly side plates 28 which are integrally provided on either side of said test stick support plate 26. The test stick support plate 26 supports a test stick 39, which is pushed against the front surface of said test stick support plate 26 by a test stick pushing member 35 which will be described hereinafter. A window hole 27 is formed through the test stick support plate 26, and a piece 40 of test paper which is mounted on the test stick 39, when said test stick 39 is thus held against the front surface of the test stick support plate 26 by the test stick pushing member 35, is confronted against said window hole 27 and thereby is exposed both to the light emitting diode 12 and to the phototransistor 14. The holder assembly side plates 28 are provided in order to prevent the test stick 39 from shifting sideways during this held condition thereof.

This test stick holder assembly 24 is mounted to the front surface of the sensor housing 10 from below in a detachable manner, as follows. Two side portions of the depression 11 of the sensor housing 10 are formed with two engagement grooves 16, and the test stick holder assembly 24, as shown in FIG. 4, is formed with two side engagement ribs 26a along the edges of the test stick support plate 26 thereof, said side engagement ribs 26a being inserted into the engagement grooves 16 from below from the point of view of FIG. 1b, thus engaging the test stick holder assembly 24 to the front surface of the sensor housing 10. On the other hand, when said test stick holder assembly 24 is to be detached from said sensor housing 10, then, with the insertion unit cover 29 which will be described hereinafter in the open condition, a suitable tool such as a coin or the like is inserted between an inclined portion 25a on the rear end of the holder assembly base 25 and a similarly inclined portion 4a of the lower case member 4, and is twisted so as to provide lever action to lever the test stick holder assembly 24 downwards as seen in FIG. 1b with respect to the sensor housing 10, with the side engagement ribs 26a sliding in the engagement grooves 16 at this time. The test stick holder assembly 24 is mounted in this fashion to the sensor housing 10, because this test stick holder assembly 24 is in direct contact with the test sticks 39 which are used for testing blood sugar levels of the subjects, and accordingly said test stick holder assembly 24 is from time to time subjected to smearing and is therefore required to be washed or otherwise cleansed fairly frequently.

However, in other preferred embodiments of the present invention, the construction of the test stick holder assembly 24 may be varied; thus, the shown construction for the test stick holder assembly 24 is not intended to be limitative of the concept of the present invention, since it is a matter of design choice.

FIG. 5 shows a perspective view of the test stick insertion unit cover 29. This insertion unit cover 29 is shaped with a cross section formed generally in the shape of a letter "C", and the rear end of the upper surface thereof is formed with an upper notch 30. This upper notch 30 is provided for receiving the test stick 39 through, as will be explained shortly with reference to FIGS. 2a and 2b. Further, the rear end of the lower surface thereof is formed with a lower notch 31, which is provided for facilitating the removal of the test stick holder assembly 24 as explained above, by exposing the holder assembly base 25 of this test stick holder assembly 24 to the outside, as shown in FIGS. 1b and 2b.

Further, on either side of the insertion unit cover 29 there are provided two side plate members 32. These side plate members 32 are provided on their outwardly facing sides with engagement portions 33. These engagement portions 33 slide in corresponding guide grooves 9a formed in the test stick insertion unit 9 and are guided thereby, as best shown in FIGS. 1a and 1b, so that said insertion unit cover 29 is slidably mounted to said test stick insertion unit 9 and thus to the case assembly 2 so as to be freely movable with respect thereto to and fro through a certain distance. Further, when said insertion unit cover 29 has moved forwards (to the right in the figures), i.e. in the henceforward so called opening direction which is denoted by the sign "O" in FIGS. 1b and 2b, with respect to the case assembly 2 through said certain distance from its extreme leftwards position with respect to said case assembly 2, then the engagement portions 33 come into contact with the ends of the guide grooves 9a, so as to prevent said insertion unit cover 29 from moving any further in said opening direction "O" with respect to said case assembly 2.

To the internal surface of the insertion unit cover 29 there is provided the previously discussed test stick pushing member 35. This test stick pushing member 35 is supported by a support member 34 which is erected from said internal surface of said insertion unit cover 29. The test stick pushing member 35, which may be made of a suitable elastic type material such as rubber, presses the tip of the test stick 39 against the test stick support plate 26, when the insertion unit cover 29 is in its closed position.

Figure 2A:
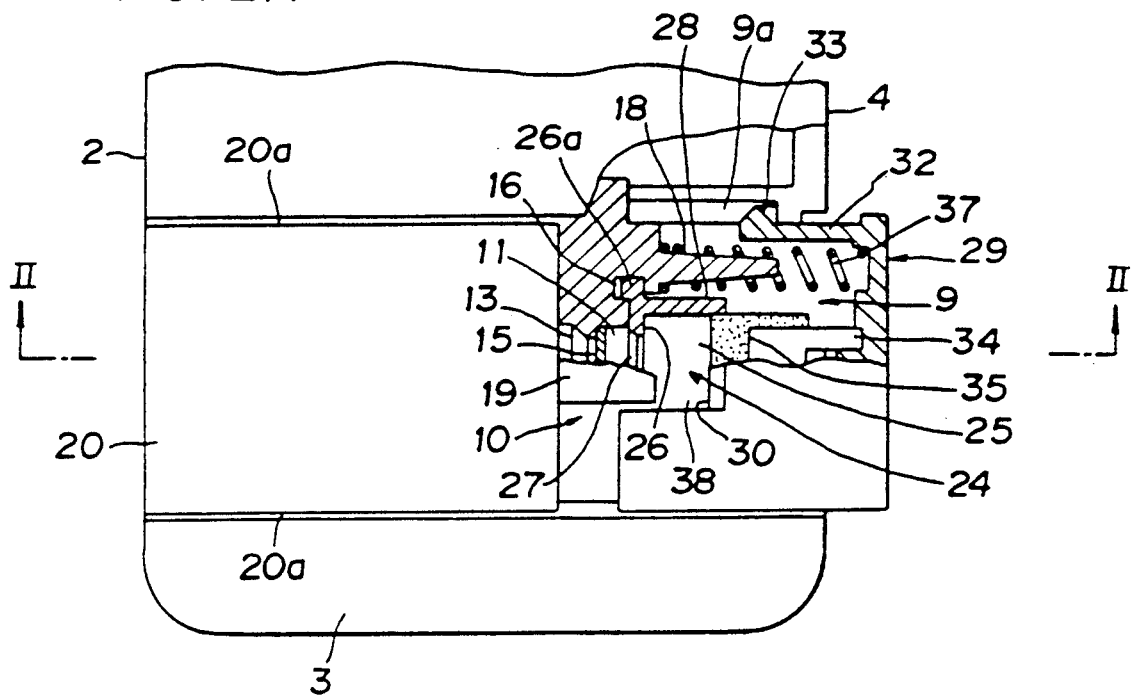
FIG. 2a is an enlarged partly broken away part sectional view, taken in the same horizontal sectional plane as FIG. 1a, of said first preferred embodiment of the chemical level measurement device of the present invention, as shown with said insertion unit cover thereof in the opened condition.
Figure 2B:
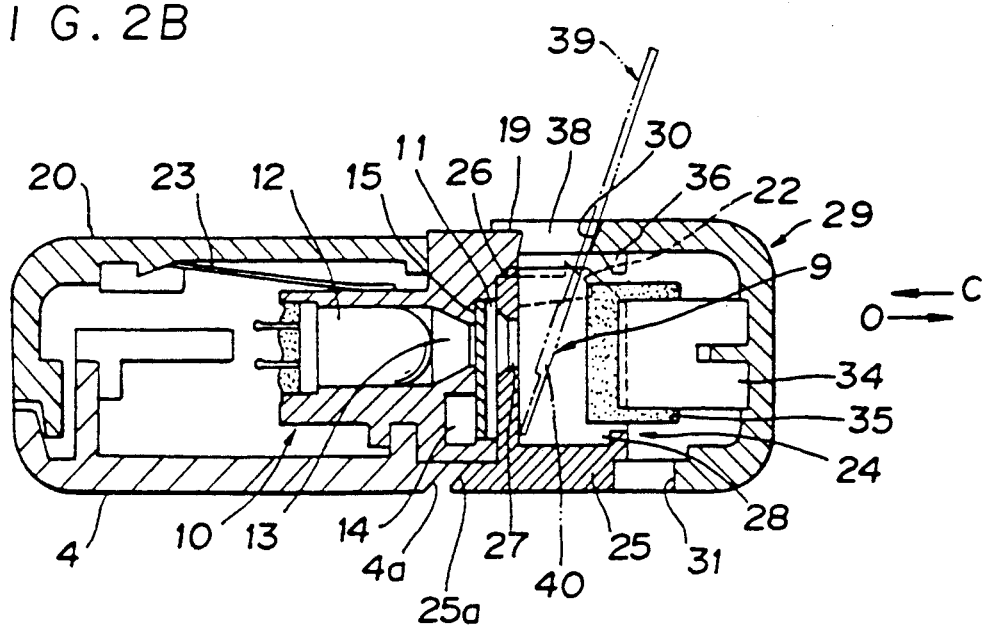
FIG. 2b is an enlarged sectional view, taken in a vertical sectional plane with regard to said preferred orientation during use and shown by the arrows II—II in FIG. 2a, of said first preferred embodiment of the chemical level measurement device of the present invention, again as shown with said insertion unit cover thereof in the opened condition, and again with a test stick inserted thereinto.

Further, to the internal surface of the insertion unit cover 29 there are provided a pair of engagement pawls 36 (referred to as "means for engaging" in the claims), as best shown in FIGS. 1b and 2b. These engagement pawls 36, when the insertion unit cover 29 is biased in the leftwards or so called closing direction, denoted by a "C" in FIGS. 1b and 2b, so as to bring it to its so called closed state, engage with the engagement rods 22 of the opening button member 20, provided that said opening button member 20 is not being pressed, and hold the insertion unit cover 29 in the aforesaid closed state thereof.

Further, a pair of compression coil springs 37 (referred to as "means for biasing" in the claims) are provided. These compression coil springs 37 are fitted over shaft portions 18 which project from the front surface of the sensor housing 10, and their one ends bear against the internal surface of the insertion unit cover 29, while their other ends bear against said front surface of said sensor housing 10. Thereby, the insertion unit cover 29 is biased in the opening direction "O", i.e. rightwards in FIGS. 1a, 2a, and 3 which show these structures to best advantage, with respect to the case assembly 2.

Finally, the test stick 39, as best shown in FIGS. 1a and 2b, consists of a thin plate like strip 39a which may be made of a synthetic resin material or the like, to the tip of which is fixed a piece 40 of test paper which is impregnated with a test chemical.

PHYSICAL OPERATION OF THIS FIRST PREFERRED EMBODIMENT

Now, an exemplary operational episode of this first preferred embodiment of the chemical level measurement device of the present invention will be described with regard particularly to the physical movements and manipulations involved, as distinct from the electronic processing steps involved in said operational episode which will be described hereinafter. This description of physical operation is given in order to facilitate understanding of the functions and advantages of the physical construction described above.

Figure 6B:
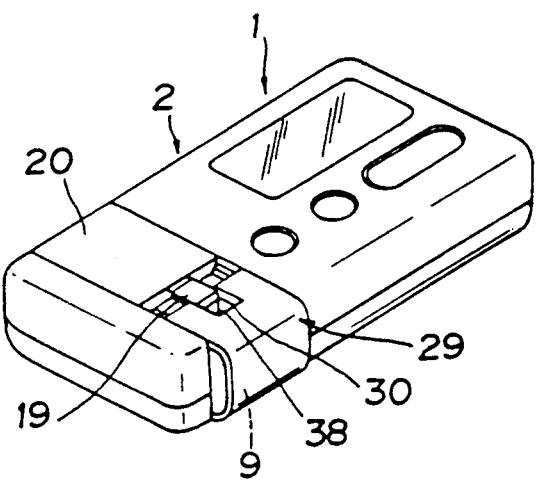
FIG. 6b is another perspective view, similar to FIG. 6a, of this first preferred embodiment of the chemical level measurement device of the present invention as a whole, shown in its state with said insertion unit cover thereof now being in the opened condition and with no test stick being inserted into its test stick insertion unit.

First, from the state of the apparatus shown in FIG. 6a in which the insertion unit cover 29 is in the closed condition thereof, the operator pushes down on the opening button member 20. This causes the engagement rods 22 with their engagement pawls to be moved in the downwards direction as seen in the figures, so that said engagement pawls become disengaged from the engagement pawls 36 of the insertion unit cover 29. As soon as this disengagement has occurred, the insertion unit cover 29 is allowed to be moved, by the biasing action of the compression coil springs 37, in the rightwards or opening direction "O" in the figures, so as to reach the position shown in FIG. 2b, at which position said rightwards or opening motion of said insertion unit cover 29 is stopped by the engagement portions 33 thereof coming into contact with the ends of the guide grooves 9a. In this state of the apparatus, a test stick insertion aperture 38 is defined between a projecting portion 19 of the sensor housing 10 and the upper notch 30 of the insertion unit cover 29. This state of the apparatus is shown in FIG. 6b.

Figure 6C:
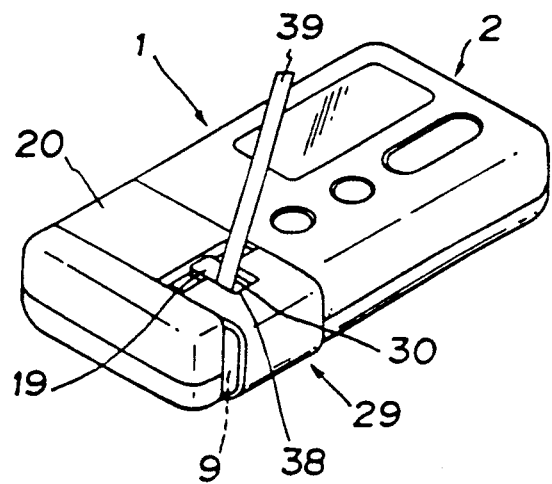
FIG. 6c is another perspective view, similar to FIGS. 6a and 6b, of this first preferred embodiment of the chemical level measurement device of the present invention as a whole, shown in its state with said insertion unit cover thereof still being in the opened condition and now with a test stick being inserted into its test stick insertion unit.

Next, as shown in FIG. 6c, after a sample of the blood of the subject has been dripped onto the test stick 39 so as to engender a coloring reaction in the test paper piece 40 thereof, the tip portion of said test stick 39 which incorporates said test paper piece 40 is poked by the operator of this first preferred embodiment of the chemical level measurement device of the present invention into this test stick insertion aperture 38, so as to reach the test stick insertion unit 9; the internal state of the apparatus in this condition is shown in FIG. 2b. In this condition, the tip of the test stick 39 is located within the test stick holder assembly 24, and particularly the test paper piece 40 opposes the window hole 27 of the test stick support plate 26.

Figure 6D:
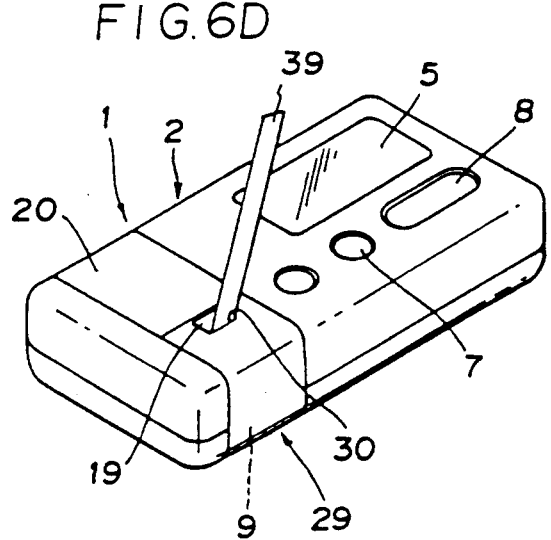
FIG. 6d is another perspective view, similar to FIGS. 6a through 6c, of this first preferred embodiment of the chemical level measurement device of the present invention as a whole, shown in its state with said insertion unit cover thereof now being in the closed condition and with a test stick still being inserted into its test stick insertion unit.

Next, the operator closes the insertion unit cover 29 to the position thereof shown in FIGS. 1a and 1b, so that the overall configuration of the device comes to be as shown in FIG. 6d. For doing this, it suffices for the operator to push on the insertion unit cover 29 in its closing direction shown in the figures as "C" with his or her finger, and this finger may conveniently be a finger of the same hand that is holding the device 1 as a whole in place on a flat surface such as a desk and is stopping said device 1 from sliding about on said flat surface. Therefore, the convenience in operation is attained that the user may practicably hold the device 1 in place and close the insertion unit cover 29 of said device 1 with one and the same hand, while holding the test stick 39 in place with his or her other hand. Accordingly the use of three hands for operating this device is not required.

As the insertion unit cover 29 is pushed in this manner in the closing direction, against the biasing force of the compression coil springs 37 which is overcome, when said insertion unit cover 29 reaches the fully closed position as shown in FIG. 6d, the engagement pawls 36 engage with the engagement pawls on the engagement rods 22 of the opening button member 20, and thereby said insertion unit cover 29 comes to be held in its closed position without being required to be further held at said closed position. This is the state of the apparatus illustrated in FIG. 1b. In this condition, the tip of the test stick 39 is being supported on the test stick support plate 26 by being pushed thereagainst by the test stick pushing member 35, while the test paper piece 40 is facing and confronting the window hole 27 of said test stick support plate 26. And the main body of the test stick 39 is being pinched between the front surface of the projecting portion 19 of the upper case member 3 and the upper notch 30 formed in the insertion unit cover 29. Because this projecting portion 19 and this upper notch 30 are formed with inclined surfaces, as suggested in the figures the test stick 39 is thereby bent slightly in the forward direction. The effect of this is that the ingress of external illumination into the test stick insertion unit 9 from the outside through any gap between the projecting portion 19 and the upper notch 30 is effectively prevented.

Next, with the device in this condition, the operator turns on the start switch 8. This causes the light emitting diode 12 to be powered so that it emits light. This light passes through the communication aperture 13, the transparent plate 15, the depression 11, and the window hole 27 to reach the surface of the test paper piece 40. Light then emitted from said surface of said test paper piece 40 passes via the window hole 27, the depression 11, and the transparent plate 15 to fall on the phototransistor 14. While this is happening, the value of the blood sugar level in the blood which has been infiltrated into the test paper piece 40 is quantitatively determined, according to the current flowing through said phototransistor 14, by an electronic measurement circuit which will be explained in detail hereinafter in the section of this specification which relates to the electronic constitution of the present invention. This blood sugar value is then displayed on the LCD display unit 5. And this value is stored in a memory in the measuring circuit, as will also be described hereinafter.

In order to remove the test stick 39 from the device after the completion of the measurement process for blood sugar, the operator need merely depress the opening button member 20, and then as described before the insertion unit cover 29 moves in the forward direction to the position thereof shown in FIG. 6c. While the apparatus is in this state, the operator pulls upwards on the free end of the test stick 39 and removes it for disposal. Then as before the operator closes the insertion unit cover 29 by pushing it with a simple operation.

Although in the above described physical construction for the first preferred embodiment of the chemical level measurement device of the present invention the insertion unit cover 29 was biased towards the opened state thereof by the biasing means (the compression coil springs 37) and was held in its closed state by the engagement means (the engagement pawls 36 and the engagement pawls on the engagement rods 22), as an alternative construction in some variant embodiment it would be possible to arrange these matters conversely, as a matter of design choice: thus, in such a case, the insertion unit cover 29 would be biased towards the closed state thereof by the biasing means, and would be held in its opened state by the engagement means. Such a construction is within the purlieu of the inventive concept of the present invention.

Further, although in the above described physical construction for the first preferred embodiment of the chemical level measurement device of the present invention the application was to a reflection type blood sugar measurement device, in which the light from the light emitting diode 12 was reflected off the test paper piece 40 to impinge on the phototransistor 14, as an alternative the present invention could be applied to a transmission type blood sugar measurement device, in which light from a means similar to said light emitting diode 12 is transmitted through a test paper or the like to impinge upon a light detecting means. Further, as a matter of course, the present invention could be applied to some other types of biochemical measurement devices, such as to an urine sugar measurement device or the like, irrespective of whether such other devices are of the reflection type or of the transmission type.

Thus it is seen that, according to such a chemical level measurement device as specified above according to the physical construction of the first preferred embodiment of the chemical level measurement device of the present invention, the action of opening the test paper insertion unit cover 29 can be accomplished simply by manipulating the engagement of the engagement releasing means, consisting of the opening button member 20. When this is done, the test paper insertion unit cover 29 is automatically opened by the biasing force supplied by the biasing means, consisting of the compression coil springs 37. Further, since the reverse action of closing the insertion unit cover 29 can simply be accomplished by pushing said test paper insertion unit cover 29 with one finger, which conveniently may be a finger of the same hand of the operator that is simultaneously holding the case assembly 2 of the device down to stop it sliding around on a surface on which it rests, thereby the operation of the device is made easy, because the other hand of the operator is left free for holding the test stick 39 in place, and accordingly it is not required for the operator to have three hands. Thus, this chemical level measurement device can be easily operated, and allows of easy and accurate placing of a test stick 39 into the test stick insertion unit 9 thereof. Further, this chemical level measurement device, while being light in weight and small in size, is not subject to moving around during use upon the surface on which it is placed, and yet during use does not require the assistance of a second operator for holding it down or the like. Accordingly, this chemical level measurement device is suitable to be used by an operator whose finger is currently in a wounded state by having been pricked for obtaining of a sample of blood for being dripped onto a test stick 39 for chemical level measurement by said device. Further, because, even when an undue stress is applied to the chemical level measurement device, concentration of stress upon the case assembly 2 thereof is reduced by being applied via the sliding engagement of the insertion unit cover 29 to the case assembly 2, as opposed to the pivoting type of engagement which was utilized in the prior art and which constituted a weak point, accordingly this chemical level measurement device is strongly built and is not subject to damage over a period of time.

ELECTRONIC STRUCTURE OF THIS FIRST PREFERRED EMBODIMENT

Now, the operation of this first preferred embodiment of the chemical level measurement device of the present invention will be explained in detail with regard to its electronic side, as opposed to its gross physical aspect which has been amply descanted on in the foregoing dissertation.

Figure 8:
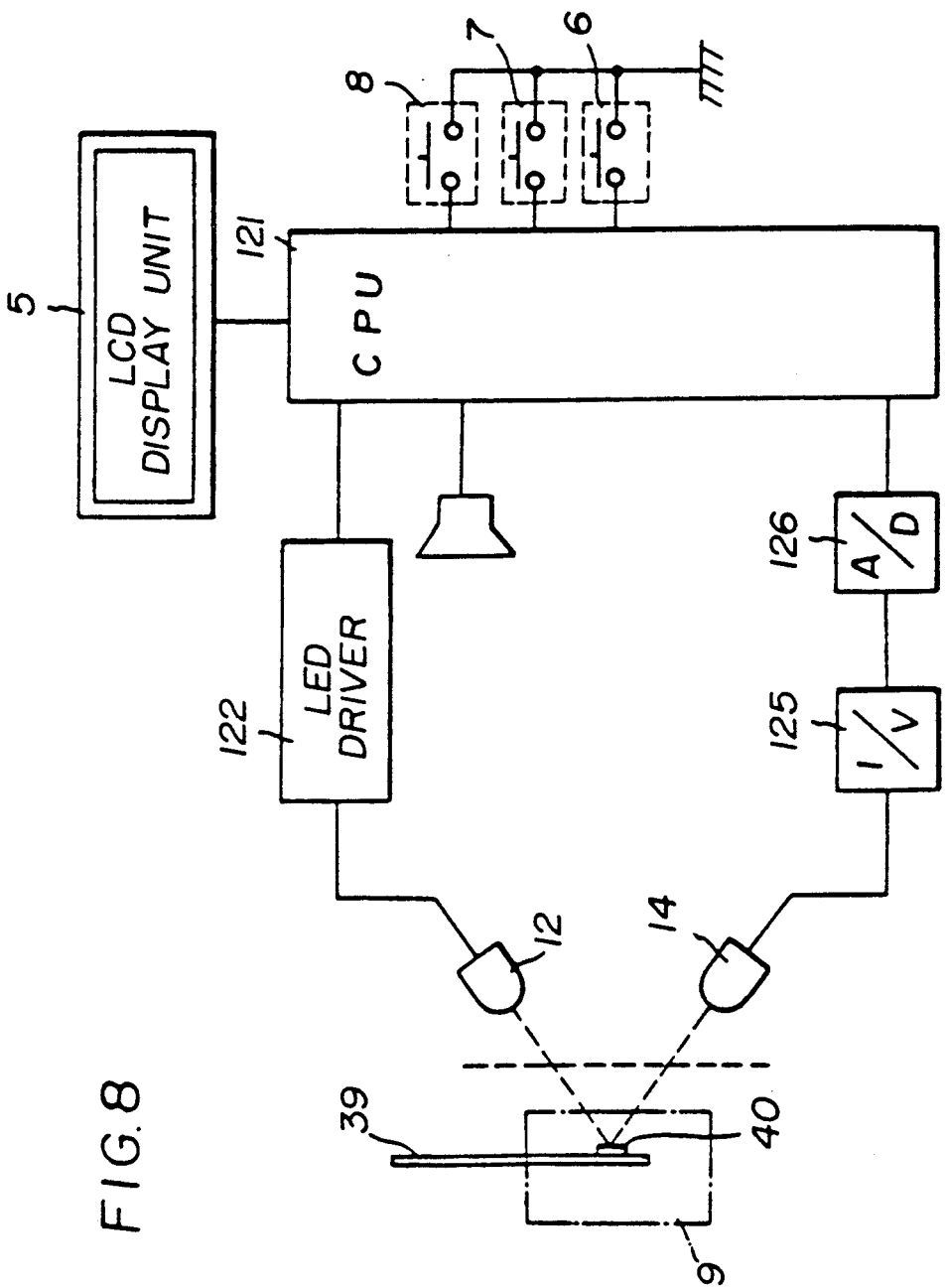
FIG. 8 is a block diagrammatical view of the electronic circuitry incorporated in the first preferred embodiment of the chemical level measurement device of the present invention.

FIG. 8 is a block diagrammatical view of the electronic circuitry incorporated in this first preferred embodiment of the chemical level measurement device of the present invention. In this figure, the reference numeral 122 denotes a drive circuit which supplies, according to a command signal from a controller 121 which will be described hereinafter, a drive electrical current to the light emitting diode 12. The light from the light emitting diode 12 falls upon the surface of the test paper piece 40 fixed on the end of the test stick 39 which is mounted in the test stick insertion unit 9, and light reflected (in this first preferred embodiment) from said test paper piece 40 is received by the phototransistor 14 and is converted to an electrical current signal. This electrical current signal is converted into a voltage signal by a current to voltage conversion circuit 125, and then this voltage signal, which is an analog signal, is converted into a digital signal by an analog to digital converter 126. This digital signal is then fed to the controller 121. Further, this controller 121 receives signals from the power switch 6, the mode switch 7, and the start switch 8, thus being apprised of whether or not the operator is currently depressing these switches. The controller 121 also controls a buzzer, not denoted by any reference numeral.

This controller 121 outputs control signals for controlling the LED driver 122 and for controlling the LCD display unit 5, according to principles which will be explained hereinafter. No concrete illustration of the structure of any particular realization of the controller 121 will be given herein, since various possibilities for the details thereof can be easily supplemented by one of ordinary skill in the electronic and computer programming art based upon the functional disclosures set out in this specification. In the first preferred embodiments of the device and the method of the present invention, the controller 121 is concretely realized as a micro computer and its associated circuitry, said micro computer operating at the behest of a control program which will not be completely detailed herein, since the details thereof which are not disclosed in this specification can likewise be easily supplemented by one of ordinary skill in the electronic and computer programming art based upon the functional disclosures set out herein. However, it should be particularly understood that such realizations in the micro computer form, although first preferred, are not the only ways in which the controller 121 can be provided; in other possible embodiments it could be constituted as an electrical device not incorporating a microprocessor. In the preferred case, however, such a microprocessor will typically comprise: a CPU (central processing unit) which obeys said control program to be described shortly and which inputs data, performs calculations, and outputs data; a ROM (read only memory) which stores said program to be described shortly and initialization data therefor and so on; and a RAM (random access memory) which stores the results of certain intermediate calculations and data and so on; and these devices together will constitute a logical calculation circuit, being joined together by a common bus which also links them to an input port and an output port which together perform input and output for the system. And the system will typically also include buffers for the electrical signals outputted from the analog to digital converter 126 and from the above detailed switches 6, 7, and 8 to the input port device, and drive circuits through which actuating electrical signals are passed from the output port device to the LED driver 122, the LCD display unit 5, and the buzzer.

SUMMARY OF THE ELECTRONIC OPERATION OF THIS FIRST PREFERRED EMBODIMENT

This controller 121 generally functions as will now be explained, so as to select various modes such as program mode, memory mode, and so on, and so as to execute a series of processing actions for the particular mode selected, as well as the functions for quantitatively determining the content of the particular chemical for which it is analyzing the body fluid of the subject, such as the blank value reading function for reading a signal when an unused test stick is mounted to the test stick insertion unit 9, a coloring reaction value reading function for observing the optical reaction of a test paper piece 40 which has been infiltrated with the body fluid of the subject, and a function of determining the concentration of the particular chemical in said body fluid of the subject by computing a reflection coefficient from the blank value and from the coloring value, and by determining the concentration of the particular chemical in said body fluid of the subject by lookup from a reference table.

Particularly, when the program mode is selected, on the LCD display unit 5 it is displayed which reference table will be utilized for lookup, and what is the program number, and every time the start switch 8 is pressed the program number is incremented and the reference table which matches with the type of test paper which is to be used in the test is selected. The controller 121 is provided with a memory in which are stored, for example, ten different sets of data corresponding to ten different such memory numbers, and thus ten new sets of data from the past to the future are stored with the corresponding memory numbers. In this mode, when a certain memory number is selected, the number of data and a corresponding average value are displayed in an alternating manner on the LCD display unit 5, and when the start switch 8 is pressed the memory number and the data value are displayed. Thereafter, every time the start switch 8 is depressed, the memory number is incremented, and the memory number and the concentration of the particular chemical are stored in the memory region for that particular memory number.

According to this first preferred embodiment of the chemical level measurement device of the present invention, every time the mode switch 7 is pressed, the measurement mode, the program mode, and the memory mode are sequentially selected in that order, and the measurement mode is then selected again.

DETAILS OF THE ELECTRONIC OPERATION OF THIS FIRST PREFERRED EMBODIMENT

FIG. 7 shows a flow chart for explaining the operation of a portion of the aforementioned control program which directs the operation of the controller 121, according to this first preferred embodiment of the chemical level measurement device of the present invention. This flow chart will now be explained; no particular programming steps for implementing said flow chart are shown or suggested in this specification, since various possibilities for the details thereof can be easily supplemented as appropriate by one of ordinary skill in the programming art, particularly when based upon the functional disclosures set out in this specification.

Figure 9:
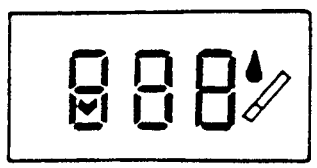
FIGS. 9A–9F is a set of illustrations for showing examples of display indications being made upon a display incorporated in said first preferred embodiment of the chemical level measurement device of the present invention.

Thus, in the FIG. 3 flow chart, when the power switch 6 is turned on the action begins, and after the START block, in the step ST1, the controller 121 initializes its memory which is used for arithmetic processes, and lights up all the sections of the LCD display unit 5 for the purpose of checking the operation of said LCD display unit 5. This state of the LCD display unit 5 is shown in FIG. 9a. Then next the flow of control passes to the decision step ST2. As shown in FIG. 9a, the display segments of the LCD display unit 5 include three character displays each with seven segments in the form of a figure "8", and also a symbol 2a representing the test stick 39, a symbol 2b representing dripping of bodily fluid onto said test stick 39, and a little symbol in the leftmost figure "8" segment combination for forming the letter "M" as will be explained hereinafter.

In this next decision step ST2, then, the controller 121 makes a decision as to whether or not the mode switch 7 is in the ON state. If the result of this decision is YES, so that indeed said mode switch 7 is currently in the ON state, then next the flow of control is transferred to the decision step ST3; but, if the result of this decision is NO, so that in fact currently said mode switch 7 is in the OFF state, then next the flow of control is transferred to the step ST5.

In the next decision step ST3, the controller 121 makes a decision as to whether or not the power switch 6 is being manipulated. If the result of this decision is YES, so that indeed said power switch 6 is currently being manipulated, then next the flow of control is transferred to the step ST4; but, if the result of this decision is NO, so that in fact said power switch 6 is not currently being manipulated, then next the flow of control is transferred to the step ST5.

In the step ST4, which is reached if and only if the power switch 6 is being manipulated while also the mode switch 7 is in the ON state, the controller 121 clears all the old data in the memory; and then next the flow of control passes to the step ST5.

On the other hand, if it is not required by the operator to clear the data in the memory, then simply said operator does not manipulate the power switch 6 while also the mode switch 7 is in the ON state, and the flow of control skips the step ST4 to pass directly to the next step ST5. In any case, in this step ST5, the controller 121 causes the stick symbol 2a on the LCD display unit 5 to blink, and displays the program number on the digit portion of said LCD display unit 5, as exemplarily shown in FIG. 9b. This example has the following meaning: the indication "P1" indicates that program number one is being used, while the blinking stick symbol 2a without the blinking drip symbol 2b indicates that the operator is being urged to mount a test stick 39 not impregnated with any bodily fluid, i.e. a blank test stick 39, in the test stick insertion unit 9. Then next the flow of control passes to the decision step ST6.

In this next decision step ST6, the controller 121 makes a decision as to whether or not the mode switch 7 is currently in the ON state. If the result of this decision is YES, so that indeed currently the mode switch 7 is in the ON state, which is done when the program mode or the memory mode is to be selected instead of the measurement mode, then next the flow of control is transferred to the step ST19; but, if the result of this decision is NO, so that currently in fact the mode switch 7 is in the OFF state, then next the flow of control is transferred to the decision step ST7, at which point it is determined that the measurement mode is to be performed.

In this next decision step ST7, the controller 121 makes a decision as to whether or not the start switch 8 is currently in the ON state. If the result of this decision is YES, so that indeed the start switch 8 is currently in the ON state, then next the flow of control is transferred to the step ST8; but, if the result of this decision is NO, so that in fact the start switch 8 is currently in the OFF state, then next the flow of control is transferred to the step ST5 again, to cycle around in a tight loop.

The user, therefore, is required to turn on the start switch 8 before proceeding to measurement. When this happens, next in the step ST8 the controller 121 measures the value of coloring or the like provided by the blank test stick 39 that it is assumed has now been placed by the operator into the test stick insertion unit 9, according to the instructions just given; this is done by the controller 121 controlling the LED driver 122 to light up the light emitting diode 12 to illuminate the blank test paper piece 40 on the end of this blank test stick 39, and by the light signal reflected from said blank test paper piece 40 and sensed by the phototransistor 14 being transmitted back to said controller 121, via the current to voltage conversion circuit 125 and the analog to digital converter 126. Then next the flow of control passes to the step ST9.

In this next step ST9, the controller 121 causes the drip symbol 2b on the LCD display unit 5 to blink. This is for urging the operator to drip some of the body fluid the concentration in which of the certain chemical is desired to be measured upon the test paper piece 40 on the end of the test stick 39, and then to insert said test stick 39 into the test stick insertion unit 9. Then the flow of control passes next to the decision step ST10.

In this next decision step ST10, the controller 121 makes a decision as to whether or not the start switch 8 is ON. If the result of this decision is YES, so that indeed said start switch 8 is currently ON, then next the flow of control is transferred to the step ST11; but, if the result of this decision is NO, so that in fact said start switch 8 is currently OFF, then next the flow of control is transferred back to the step ST9 again, to continue flashing the drip symbol 2b on the LCD display unit 5 until the operator does indeed perform his or her duty and does insert the test stick 39 infiltrated with bodily fluid into the test stick insertion unit 9 and does indeed press the start switch 8.

In this step ST11, the controller 121 performs a count down of, exemplarily, approximately 50 seconds, i.e. waits for approximately 50 seconds; and then next the flow of control passes to the step ST12. This time period is allowed to elapse in order to allow the test chemical, previously impregnated into the test paper piece 40, to react with the certain chemical in the bodily fluid thus infiltrated into said test paper piece 40, to produce an optical reaction such as a change of color.

In the next step ST12, the controller 121 measures the value of coloring or the like provided by the now impregnated and reacted test stick 39 that it is assumed has now been placed by the operator into the test stick insertion unit 9, according to the instructions just given; as before, this is done by the controller 121 controlling the LED driver 122 to light up the light emitting diode 12 to illuminate the now impregnated and reacted test paper piece 40 on the end of this test stick 39, and by the light signal reflected from said blank test paper piece 40 and sensed by the phototransistor 14 being transmitted back to said controller 121, via the current to voltage conversion circuit 125 and the analog to digital converter 126. Then next the flow of control passes to the step ST13.

In this step ST13, the controller 121 calculates a reflection coefficient from this reacted test stick color value and from the blank test stick color value that was determined previously in the step ST8 and was stored in the memory, and further said controller 121 calculates a value for the concentration of the certain chemical in the bodily fluid of the subject from this reflection coefficient and from the current reference table; and then next the flow of control passes to the step ST14.

In this step ST14, the controller 121 displays this concentration value upon the LCD display unit 5, which completes the process of determining the concentration of the certain chemical; and then next the flow of control passes to the decision step ST15.

In this next decision step ST15, the controller 121 makes a decision as to whether or not the start switch 8 is currently in the ON state. If the result of this decision is YES, so that indeed the start switch 8 is currently in the ON state, then next the flow of control is transferred back to the step ST5 again, to cycle around in a closed loop, and the system stands by for the next measurement process episode; but, if the result of this decision is NO, so that in fact the start switch 8 is currently in the OFF state, then next the flow of control is transferred to the decision step ST16.

In this next decision step ST16, the controller 121 makes a decision as to whether or not the mode switch 7 is currently in the ON state. If the result of this decision is YES, so that indeed currently the mode switch 7 is in the ON state, then next the flow of control is transferred to the step ST17; but, if the result of this decision is NO, so that currently in fact the mode switch 7 is in the OFF state, then next the flow of control is transferred back to the step ST14 again, to cycle around in a tight loop while continuing to displays the concentration value upon the LCD display unit 5.

Figure 9F:
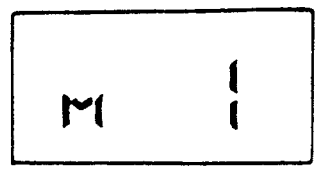
Figure 9B:
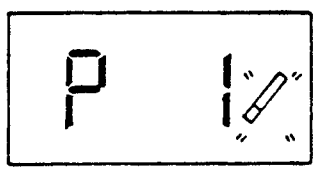
Figure 9G:
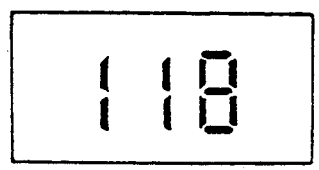
Figure 9C:
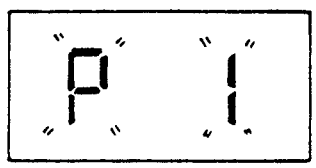
Figure 9H:
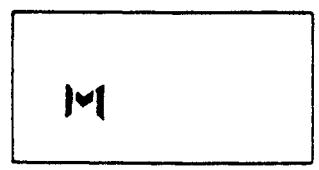

In the next step ST17, the controller 121 records the concentration value in the memory, and illuminates the symbol "M" on the LCD display unit 5 as shown in FIG. 9h, in order to indicate as much; and then next the flow of control passes to the decision step ST18. Thus, since the measured concentration value is stored in the memory only when the mode switch 7 is turned ON, only the necessary and appropriate measurement data are stored in the memory. As described above, the controller 121 can store in its memory the last ten measurement data in order of occurrence. Therefore, when a new measurement data is obtained and the mode switch 7 is turned ON, the current data is stored in memory as the newest measurement data and the other past stored data are shifted down by one position, with the result that the tenth most recent measurement data are pushed down and are cleared out of memory. In the next decision step ST18, the controller 121 makes a decision as to whether or not the start switch 8 is currently turned ON. If the result of this decision is YES, so that indeed said start switch 8 is currently turned ON, then next the flow of control is transferred back to the step ST5 again, to cycle around in a loop and to be ready for the next measurement episode; but, if the result of this decision is NO, so that in fact said start switch 8 is currently turned OFF, then next the flow of control is transferred back to this decision step ST18 again, to cycle in a tight closed loop until in fact said start switch 8 comes to be turned ON.

On the other hand, in the ST5 state, i.e. when the number of the program being utilized and also the stick symbol 2a are flashing as shown in FIG. 9b, if the operator desires to proceed to a subsequent program mode, he or she pushes the mode switch 7 to turn it ON. In such a case, from the decision step ST6 the decision is now YES, so that the flow of control passes to the step ST19. In this step ST19, the controller 121 displays the program number (only; the stick symbol 2a is now not illuminated) by blinking said program number on the LCD display unit 5, as exemplarily shown in FIG. 9c which is exemplarily indicating by the blinking indication "P1" that currently the first table is the reference table; and then next the flow of control passes to the decision step ST20.

In this next decision step ST20, the controller 121 makes a decision as to whether or not the mode switch 7 is currently in the ON state. If the result of this decision is YES, so that indeed currently the mode switch 7 is in the ON state, which is done when the memory mode is to be selected instead of the program mode, then next the flow of control is transferred to the step ST23; but, if the result of this decision is NO, so that currently in fact the mode switch 7 is in the OFF state, then next the flow of control is transferred to the decision step ST21, at which point it is determined that the program mode is (still) to be performed.

In this next decision step ST21, the controller 121 makes a decision as to whether or not the start switch 8 is currently in the ON state. If the result of this decision is YES, so that indeed the start switch 8 is currently in the ON state, then next the flow of control is transferred to the step ST22; but, if the result of this decision is NO, so that in fact the start switch 8 is currently in the OFF state, then next the flow of control is transferred to the step ST19 again, to cycle around in a tight loop.

In this next step ST22, the controller 121 increments the program number; and then next the flow of control passes to the step ST19 again, so as to now display this incremented program number, "P2" in the initial instance. This exemplary display indicates that now the second table is the reference table. Thereafter, every time the start switch 8 is pressed to turn it ON, the program number is incremented, and this incremented program number is displayed on the LCD display unit 5. At each time point, the displayed program number corresponds to the selected reference table. Therefore, during measurement, if the program number is recorded for each lot of test paper that is going to be used, then it is possible to match up the lot of the test paper piece that is currently being used and the stored reference table, with the result that correct measurement will be possible.

However, if at the stage of the decision step ST20 the operator turns ON the mode switch 7, then the result of the decision will be YES, and the flow of control will pass to the decision step ST23. In this next decision step ST23, the controller 121 makes a decision as to whether or not the current table number is zero. If the result of this decision is YES, so that indeed the current table number is zero and no past data exists in the memory (in this case "A0" will be displayed on the LCD display unit 5 although such a case is not shown in any of the FIG. 9 views), then next the flow of control is transferred to the decision step ST33; but, if the result of this decision is NO, so that in fact the current table number is not zero and accordingly some past data exists in the memory, then next the flow of control is transferred to the step ST24.

In the decision step ST33, the controller 121 makes a decision as to whether or not the mode switch 7 is ON. If the result of this decision is YES, so that indeed said mode switch 7 is currently ON, then next the flow of control is transferred back to the step ST5 again, and the operational mode of the device is switched to the measurement mode; but, if the result of this decision is NO, so that in fact said mode switch 7 is OFF, then the flow of control loops back directly to this decision step ST33 again in a tight loop until in fact the mode switch 7 is turned ON.

On the other hand, if the number of data in the memory is not zero, i.e. past data exists in the memory, then in the step ST24 the controller 121 computes an average value of the data; and then next the flow of control passes to the step ST25.

Figure 9D:
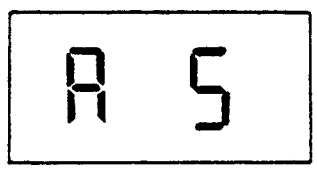
Figure 9E:

Next, in this step ST25, the controller 121 alternatingly displays on the LCD display unit 5 the number of the data, and the average value of the data. For example, if there are five data in all, and the average value thereof is 120 mm/deciliter, then the display "A5" as shown in FIG. 9d and the display "120" as shown in FIG. 9e are alternatingly displayed at a certain frequency on the LCD display unit 5, as being the data number and the average data. Then, in this state, next the flow of control passes to the decision step ST26.

In this next decision step ST26, the controller 121 makes a decision as to whether or not the mode switch 7 is currently in the ON state. If the result of this decision is YES, so that indeed currently the mode switch 7 is in the ON state, which is done when the memory mode is to be exited, then next the flow of control is transferred back to the step ST5; but, if the result of this decision is NO, so that currently in fact the mode switch 7 is in the OFF state, then next the flow of control is transferred to the decision step ST27.

In this next decision step ST27, the controller 121 makes a decision as to whether or not the start switch 8 is currently in the ON state. If the result of this decision is YES, so that indeed the start switch 8 is currently in the ON state, then next the flow of control is transferred to the step ST28; but, if the result of this decision is NO, so that in fact the start switch 8 is currently in the OFF state, then next the flow of control is transferred to the step ST25 again, to cycle around in a tight loop and to repeat the alternating display of the number of the data and the average value of the data in said step ST25.

However, if the start switch 8 is turned ON again, then from the step ST27 the flow of control passes to the step ST28. In this step ST28, the controller 121 alternatingly displays on the LCD display unit 5 the memory number, and the value of the concentration of the certain chemical. For example, if the memory number is 1, and the concentration of the certain chemical is 118 mm/deciliter, then the display "M1" as shown in FIG. 9f and the display "118" as shown in FIG. 9g are alternatingly displayed at a certain frequency on the LCD display unit 5, as being the memory number and the concentration value. Then, in this state, next the flow of control passes to the decision step ST29.

In this next decision step ST29, the controller 121 makes a decision as to whether or not the mode switch 7 is currently in the ON state. If the result of this decision is YES, so that indeed currently the mode switch 7 is in the ON state, then next the flow of control is transferred back to the step ST5; but, if the result of this decision is NO, so that currently in fact the mode switch 7 is in the OFF state, then next the flow of control is transferred to the decision step ST30.

In this next decision step ST30, the controller 121 makes a decision as to whether or not the start switch 8 is currently in the ON state. If the result of this decision is YES, so that indeed the start switch 8 is currently in the ON state, then next the flow of control is transferred to the decision step ST31; but, if the result of this decision is NO, so that in fact the start switch 8 is currently in the OFF state, then next the flow of control is transferred to the step ST28 again, to cycle around in a tight loop and to repeat the alternating display of the number of the memory and of the concentration value in said step ST28.

Thus, if the memory mode is to be executed in this state, since the mode switch 7 is normally not going to be turned ON, the result of the decision in the decision step ST29 is NO, and as long as the start switch 8 is not turned ON the result of the decision in the decision step ST30 continues to be NO, and therefore the flow of control continues to return to the step ST28, and the alternating display of the number of the memory and of the concentration value is repeated in this step ST28. If, however, the operator wants to refer to the data of the next memory region, then he or she depresses the start switch 8 so as to turn it ON. As a result, the result of the decision in the decision step ST30 is YES, and the flow of control passes to the decision step ST31. In this next decision step ST31, the controller 121 makes a decision as to whether or not the memory number agrees with the number of the data, or in other words whether or not the last data has been read. If the result of this decision is YES, so that indeed the memory number agrees with the number of data, then next the flow of control is transferred back to the step ST23, to loop around again; but, if the result of this decision is NO, so that in fact the memory number does not agree with the number of data, then next the flow of control is transferred to the step ST32.

And, in this step ST32, at which point it is determined that the last data has not been read, the controller 121 increments the memory number; and then next the flow of control passes back to the step ST28 again, to loop around in a tight loop, so that again the alternating display of the number of the memory and of the concentration value is repeated. In this case, since the memory number has been incremented, the memory number display is altered from "M1" to "M2", and the concentration of the certain chemical from the memory region M2 is read out. And, as before, the alternating display of the number of the memory and of the concentration value of the certain chemical is repeated. Thereafter, every time the start switch 8 is turned ON, the memory number is incremented, and the corresponding data is displayed in a sequential manner. Therefore, the operator of this first preferred embodiment of the chemical level measurement device of the present invention can sequentially read out the past data corresponding to the various memory regions, and can confirm the measured values.

Now, in the above described first preferred embodiment of the chemical level measurement device of the present invention, the action of switching the modes consisted of shifting between three modes—the measurement mode, the program mode, and the memory mode—in a sequential manner; but the concept of the present invention is not to be considered as being limited to this. For example, the action modes can be omitted as desired, and other modes such as an external communication mode, a check mode, a calibration mode, and so on can be appropriately combined. All such variations should be considered as being within the scope of the present invention.

Further, this concept can be, as a matter of course, applied to the measurement of any of a wide range of chemicals (such as sugar or the like) in any of a wide range of bodily fluids of a subject (such as blood or urine or the like). Again, all such variations should be considered as being within the scope of the present invention.

Thus, according to such a chemical level measurement device as described above according to the first preferred embodiment of the chemical level measurement device of the present invention, since the three various action modes may be selected between by the use of only one means, i.e. the mode selection means which is simply the mode switch 7, thereby selection between the three modes thereof may be made in a simple fashion by actuating only one button, the mode switch 7, therefore without requiring the provision of a large plurality of keys, and without requiring a large space for the mounting of control keys. Accordingly, this chemical level measurement device is low in manufacturing cost, also is convenient to use, and further meets the diversified requirements of users.

THE SECOND PREFERRED EMBODIMENT

Next, with regard to FIG. 10 which is a flow chart of the action thereof, the second preferred embodiment of the chemical level measurement device of the present invention will be described with regard to its operation. It should be understood that this second preferred embodiment of the chemical level measurement device of the present invention is substantially similar in its physical construction to the first preferred embodiment detailed above, except that, instead of the two switches provided in said first preferred embodiment, i.e. the mode switch 7 and the start switch 8, instead in this second preferred embodiment there are provided three switches: a mode switch, a select switch, and a start switch. Accordingly, no particular figure relating to the physical construction of this second preferred embodiment will be given, in view of the desirability of terseness of description. Further, the flow chart of FIG. 10, and the description thereof, are somewhat abbreviated herein as compared with the FIG. 7 flow chart and description thereof which related to the first preferred embodiment, because the operation of this second previous embodiment will easily be understood based upon these descriptions and by analogy with the operation of the first preferred embodiment.

First, in the measurement mode, the following steps are performed:

(1) When the mode key is depressed, the power is turned on and the measurement mode is entered into. At this time, the indication "888 */" is displayed immediately after the mode is manipulated, and then after a certain determinate time interval has elapsed the indication "523 */" is exemplarily displayed. "523" is the exemplary number of the reference table.

(2) As the start key is depressed, time is counted. Here, the "1" of the indication "1*" means that one second has elapsed since the start key was depressed, and the "*" of said indication means that the operator is being urged to infiltrate the bodily fluid into the test stick.

(3) 60 seconds later, an indication of "60*/" is displayed, meaning that the operator is being urged to wipe off the bodily fluid from the test stick.

(4) 61 seconds later, an indication of "61*" is displayed, meaning that the operator is being urged to insert the test stick into the test stick insertion unit 9.

(5) 120 seconds after mounting the test stick, a measurement value of "235" is displayed.

(6) If the measurement is to be continued, the operator pushes the start key, while if the measurement is to be completed the operator pushes the mode key, which disconnects the power from this measurement device.

Next, in the memory mode, the following steps are performed:

(1) After the power is turned on, and the indication "523*/" is exemplarily displayed, pushing the mode key causes the indication "A8" to be displayed. This means that data are stored from m1 to m8, and the average of the eight data is going to be produced. m1 through m8 denote the identification numbers of the memory area, and each area stores one data.

(2) After the indication "A8" is displayed, the exemplary average value "120" is displayed.

(3) And, as long as the start key is not depressed the indication "A8" and the exemplary average value "120" are repeatedly and alternatingly displayed at an appropriate frequency.

(4) When the start key is depressed, an indication of "m1" is displayed, and one second (exemplarily) later the exemplary indication "165" of the contents is displayed. In this case, also, the alternating of these displays is continued until the start key is pressed.

(5) When the start key is again depressed, an indication of "m2" is displayed, and one second (exemplarily) later the exemplary indication "204" of the contents is displayed. In this case, also, the alternating of these displays is continued until the start key is pressed yet again.

This procedure is repeated each time the start key is pressed, through "m20".

(6) If, however, this memory mode is to be terminated and the coding mode is to be started, then the operator pushes the mode key, and the coding mode is invoked, and an exemplary indication of "523" is displayed.

Next, in the coding mode for changing the reference table, the following steps are performed:

(1) First, the indication "523*/" is exemplarily displayed as described proximately above.

(2) Pushing the select key designates the first digit of this indication "523".

(3) When the start key is depressed, a desired digit, in this case "1", is set up in this first digit.

(4) Pushing the select key again this time designates the second digit.

(5) When the start key is depressed, a desired digit, in this case the same digit as the existing digit, is set up in this second digit.

(6) Pushing the mode key after setting up a desired reference table turns off the power. In this case, one may push the mode switch immediately after the first digit is set up.

CONCLUSION

It is acceptable, according to the principle of the present invention, if the constructional and operational details of the system are varied, although the shown ones are considered to be preferred. Therefore, although the present invention has been shown and described in terms of the preferred embodiments thereof, and with reference to the appended drawings, it should not be considered as being particularly limited thereby, since the details of any particular embodiment, or of the drawings, could be varied without, in many cases, departing from the ambit of the present invention. Accordingly, the scope of the present invention is to be considered as being delimited, not by any particular perhaps entirely fortuitous details of the disclosed preferred embodiments, or of the drawings, but solely by the scope of the accompanying claims, which follow.

What is claimed is:

1. A device for measuring an amount of a certain chemical in a liquid which has infiltrated a piece of test medium impregnated with a test chemical having optical properties which alter according to the amount of the certain chemical, comprising:
   (a) a casing;
   (b) test medium insertion means provided in the casing;
   (c) a test medium holder provided in the test medium insertion means;
   (d) means for emitting light onto a test medium and located opposite the test medium holder;
   (e) means for sensing light coming from the test medium and opposite the test medium holder, which produces an output signal indicative of the optical properties of the test medium;
   (f) a cover for the test medium insertion means slidably mounted on the casing so that the cover will slidably move to cover the test medium insertion means when the test medium insertion means cover is in a closed position, and to expose the test medium insertion menas when the test medium insertion means cover is in an opened position;
   (g) means for biasing the test medium insertion cover in one sliding direction thereof;
   (h) means for engaging the test medium insertion means cover in an extreme position in a direction opposite to the one sliding direction thereof; and
   (i) means for releasing the engagement of the engaging means from the test medium insertion cover.

2. A chemical level measurement device according to claim 1, wherein the releasing means comprises a press button mounted on the casing and connected to the engaging means so as to release the test medium insertion means cover when the press button is pressed.

3. A chemical level measurement device according to claim 1 or claim 2, wherein the test medium holder is slidably mounted to the test medium insertion means and is selectively detachable therefrom.

4. A chemical level measurement device according to claim 1, further comprising:
   means for selecting between an action mode for measuring the amount of a certain chemical and at least one other mode for performing a function other than measuring the amount of the certain chemical, said selecting means comprising a push-button mode switch, the modes being switched every time the mode switch is pressed.

5. A chemical level measurement device according to claim 4, wherein at least three such modes are provided, and the three modes are switched between in a cyclical sequence, every time the mode switch is pressed.

6. A chemical level measurement device according to claim 4, wherein said selecting means can select a memory mode, said device further comprising means for displaying an identification number of a memory region corresponding to a measured value of the amount of said certain chemical, and for subsequently displaying the measured value of the amount of said certain chemical, when in the display mode.

7. A chemical level measurement device according to claim 4, further comprising means for displaying indications to an operator for urging infiltration of a liquid onto a piece of test medium.

8. A chemical level measurement device according to claim 4, further comprising means for sequentially changing data relevant to a particular mode, said sequential changing means actuated after the mode selection switch is pressed to select a mode.

9. A chemical level measurement device according to claim 5, wherein the selecting means can select a memory mode, the device further comprising means for displaying an identification number of a memory region corresponding to a measured value of the amount of the certain chemical, and for subsequently displaying the measured value of the amount of a certain chemical, when in the display mode.

10. A chemical level measurement device according to claim 5, further comprising means for displaying indications to an operator for urging infiltration of a liquid onto a piece of test medium.

11. A chemical level measurement device according to claim 5, further comprising means for sequentially changing data relevant to a particular mode, said sequential changing means actuated after the mode selection switch is pressed to select a mode.

* * * * *